United States Patent [19]  [11] Patent Number: 5,139,786
Ferrini et al.  [45] Date of Patent: Aug. 18, 1992

[54] TOPICAL FORMULATIONS

[75] Inventors: Pier G. Ferrini, Binningen; Carlo Voellmy, Rheinfelden, both of Switzerland; Peter H. Stahl, Freiburg, Fed. Rep. of Germany; Jonathan Green, Arlesheim, Switzerland

[73] Assignees: Ciba-Geigy Corporation, Ardsley, N.Y.; Henkel Kommanditgesellschaft auf Aktien, Dusseldorf-Holthausen, Fed. Rep. of Germany

[21] Appl. No.: 814,218

[22] Filed: Dec. 20, 1991

Related U.S. Application Data

[63] Continuation of Ser. No. 742,445, Aug. 5, 1991, abandoned, which is a continuation of Ser. No. 546,340, Jun. 29, 1990, abandoned.

[30] Foreign Application Priority Data

Jul. 7, 1989 [CH] Switzerland .................. 2795/89

[51] Int. Cl.$^5$ ............................................. A61F 13/00
[52] U.S. Cl. .................................... 424/449; 424/448; 514/102
[58] Field of Search ................. 424/448, 449; 514/102

[56] References Cited

U.S. PATENT DOCUMENTS

| | | | |
|---|---|---|---|
| 3,683,080 | 8/1972 | Franck | 424/204 |
| 3,962,432 | 6/1976 | Schmidt-Dunker | 424/204 |
| 4,054,598 | 10/1977 | Blum et al. | 260/502.5 |
| 4,086,334 | 4/1978 | Schmidt-Dunker et al. | 424/177 |
| 4,134,969 | 1/1979 | Schmidt-Dunker | 424/49 |
| 4,234,645 | 11/1980 | Gunther et al. | 424/204 |
| 4,304,734 | 12/1981 | Jary et al. | 260/502.5 |
| 4,327,039 | 4/1982 | Blum et al. | 260/502.5 |
| 4,597,961 | 7/1986 | Etscorn | 424/28 |
| 4,610,692 | 9/1986 | Eitenmuller et al. | 424/423 X |
| 4,634,691 | 1/1987 | Hedglin et al. | 514/108 |
| 4,666,895 | 5/1987 | Bosies et al. | 514/108 |
| 4,675,009 | 6/1987 | Hymes et al. | 424/448 X |
| 4,687,767 | 8/1987 | Bosies et al. | 514/89 |
| 4,687,768 | 8/1987 | Benedict | 514/102 |
| 4,695,465 | 9/1987 | Kigasawa et al. | 424/449 |
| 4,761,406 | 8/1988 | Flora et al. | 424/204 |
| 4,777,163 | 10/1988 | Bosies et al. | 514/80 |
| 4,871,720 | 10/1989 | Jaeggi | 514/79 |
| 4,877,618 | 10/1989 | Reed, Jr. | 424/448 |
| 4,927,814 | 5/1990 | Gall et al. | 514/108 |
| 4,929,606 | 5/1990 | Jaeggi | 514/80 |
| 4,939,130 | 7/1990 | Jaeggi et al. | 514/94 |
| 4,942,036 | 7/1990 | Geho et al. | 424/425 |
| 4,942,157 | 7/1990 | Gall et al. | 514/108 |
| 4,971,958 | 11/1990 | Bosies et al. | 514/89 |

FOREIGN PATENT DOCUMENTS

| | | |
|---|---|---|
| 890453 | 3/1982 | Belgium . |
| 0186405 | 7/1986 | European Pat. Off. . |
| 2358153 | 7/1977 | France . |
| WO8800829 | 2/1988 | PCT Int'l Appl. . |
| 1582694 | 7/1977 | United Kingdom . |

OTHER PUBLICATIONS

J. of Investigative Dermatologie 44, 339–344 (1985).
Physiological Reviews 51, 16–23 (1971).

Primary Examiner—Thurman K. Page
Assistant Examiner—D. Gabrielle Phelan
Attorney, Agent, or Firm—Irving M. Fishman; Karen G. Kaiser

[57] ABSTRACT

The invention relates to topically administrable pharmaceutical preparations containing pharmaceutically acceptable methanediphosphonic acid derivatives of formula $$\begin{array}{c} R_1 \\ \phantom{R}\diagdown \\ \phantom{R}\phantom{xx}N-CH_2-CH_2-C(OH)(PO_3H_2)_2 \\ \phantom{R}\diagup \\ R_2 \end{array} \quad (I)$$

and their salts, wherein $R_1$ and $R_2$ are hydrogen or $C_1$–$C_3$alkyl.

6 Claims, No Drawings

TOPICAL FORMULATIONS

This application is a continuation of application Ser. No. 742,445, filed Aug. 5, 1991, now abandoned. which is a continuation of Ser. No. 546,340, filed Jun. 29, 1990, now abandoned.

It is known that representatives of a class of synthetic methanediphosphonic acid derivatives are used, for example, in the treatment of osteolytic bone metastases and hypercalcaemia, since they are able to inhibit the growth and decomposition of hydroxyapatite. These compounds thus prevent bone resorption by binding spontaneously to the hydroxyapatite of the bone, so that osteoclasts, for example, are unable to cleave further hydroxyapatite crystals. Compounds of this class of substances are described, for example, in DE-OS 2,405,254.

It is known that corresponding methanediphosphonic acid derivatives are absorbed to only a small extent following oral administration, especially if food is given at the same time. In order to achieve the desired therapeutic effect, correspondingly higher doses must be administered.

Because of the importance of this class of substances in the treatment of, for example, osteoporosis, Paget's disease, Bechterew's disease and the formation of bone metastases, many attempts are being made to provide a pharmaceutical form of administration from which the active ingredients can readily be absorbed irrespective of whether food is given.

The methanediphosphonic acid derivatives used in accordance with the invention, which contain two dissociable acid groups and a basic centre, are known to exist in ionic form. F. N. Marzulli et al., The Journal of Investigative Dermatology 44, 339–344 (1965), studied the penetration of radioactively labelled organic phosphoric acid esters and phosphoric acid in vitro through human Stratum corneum and found that ionised phosphoric acid is able to pass through the skin to only an extraordinarily small extent. The conclusion drawn from these studies was that neutral molecules pass through the barrier of the Stratum corneum relatively easily, while ionic forms are able to penetrate only to a very small extent and with great difficulty. This view is shared by R. J. Scheuplein, Physiological Reviews 51, 16–23 (1971), who concludes that ionisation drastically reduces skin permeation.

Even more surprising is the discovery that pharmaceutically acceptable methanediphosphonic acid derivatives, especially those of formula I below, are readily conveyed through the skin and can thus immediately act systemically. These unexpected discoveries were made during in vitro studies to determine percutaneous absorption properties by the method of A. S. Bhatti et al., J. Pharm. Pharmacol., 40, 45 P (1988). In these studies, corresponding diffusion cells having a cell surface area of 1.27 cm$^2$ and pig skin as the membrane were used as a model for human skin. The studies showed that significant therapeutic amounts of active ingredient diffused through the membrane. These results were confirmed in studies of the in vitro transdermal absorption of bisphosphonates. Experiments were carried out on guinea pigs using $^{14}$C-labelled active ingredient. 6 mg of cold bisphosphonate active ingredient and approximately $10^6$ dpm of $^{14}$C-labelled bisphosphonate in 200 μl of 2% Klucel in distilled water having a pH of 7.5 were applied to a shaved area of 3×5 cm, and the area was covered with an occlusive dressing. The radioactive material in the excreted urine was measured after 1, 2 and 3 days.

The present invention relates to topically administrable pharmaceutical preparations containing pharmaceutically acceptable methanediphosphonic acid derivatives or salts thereof, to their manufacture and use.

Suitable methanediphosphonic acid derivatives having pharmaceutical activity are, for example, compounds of formula

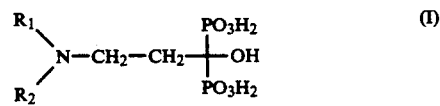

and their salts, wherein $R_1$ and $R_2$ are hydrogen or $C_1$–$C_3$alkyl.

Salts of compounds of formula I are especially their salts with bases, such as metal salts derived from groups Ia, Ib, IIa and IIb of the Periodic Table of Elements, for example alkali metal salts, especially sodium or potassium salts, alkaline earth metal salts, especially calcium or magnesium salts, and also ammonium salts with ammonia or organic amines. $C_1$–$C_3$alkyl is methyl, ethyl, n-propyl and isopropyl.

The compounds of formula I and their salts are described, for example, in DE-OS 2,405,254.

The methanediphosphonic acid derivatives of formula I have valuable pharmacological properties. In particular, they have a pronounced regulatory effect on the calcium metabolism of warm-blooded animals. They also bring about a marked inhibition of bone resorption in rats, which can be demonstrated both in the test arrangement according to Acta Endocrinol. 78, 613–24 (1975) and in the TPTX (thyroparathyroidectomised) rat model by means of experimental hypercalcaemia induced by vitamin D$_3$. Likewise, tumour hypercalcaemia induced by Walker-256 tumours is inhibited following peroral administration. Furthermore, in adjuvant arthritis in rats they exhibit a pronounced inhibition of the progress of chronic-arthritic processes in the test arrangement according to Newbould, Brit. J. Pharmacology 21, 127 (1963) and according to Kaibara et al., J. Exp. Med. 159, 1388–96 (1984). They are therefore excellently suitable as active ingredients in medicaments for the treatment of diseases that can be associated with disorders of the calcium metabolism, for example inflammatory processes in joints and degenerative processes in articular cartilage, and osteoporosis, periodontitis, hyperparathyroidism and calcium deposits in blood vessels or on prosthetic implants. They have a favourable effect both on diseases in which abnormal deposition of difficultly soluble calcium salts is observed, such as diseases of the arthritis type, for example Bechterew's disease, neuritis, bursitis, periodontitis and tendinitis, fibrodysplasia, osteoarthritis or arteriosclerosis, and on diseases involving abnormal degeneration of hard body tissue, such as hereditary hypophosphatasia, degenerative processes in articular cartilage, osteoporoses of various origins, Paget's disease and Osteodystrophia fibrosa, as well as osteolytic processes caused by tumours, and hypercalcaemia.

The invention relates especially to topically administrable pharmaceutical preparations that contain a pharmaceutically effective methanediphosphonic acid selected from the following compounds of formula I:

3-amino-1-hydroxypropane-1,1-diphosphonic acid,
3-dimethylamino-1-hydroxypropane-1,1-diphosphonic acid and
3-(N-methyl-N-n-propylamino)-1-hydroxypropane-1,1-diphosphonic acid, or a pharmaceutically acceptable salt thereof.

The invention relates also to a process for the manufacture of the topically administrable pharmaceutical preparations according to the invention, which process may be carried out in accordance with methods known per se and comprises processing a pharmaceutically acceptable methane diphosphonate derivative with customary pharmaceutically acceptable adjuncts and additives.

The invention relates further to a method of increasing the absorption of pharmaceutically acceptable methanediphosphonic acid derivatives, especially of compounds of formula I, which comprises incorporating a compound of formula I or a salt thereof into a pharmaceutical composition for topical administration.

The invention relates specifically to the pharmaceutical preparations described in the Examples and to processes for the manufacture thereof.

Depending on the starting materials and procedures chosen, the compounds of formula I may be in the form of one of the possible isomers or in the form of a mixture thereof, for example in the form of optical isomers, such as enantiomers or diastereoisomers, or geometrical isomers, such as cis-trans isomers. The optical isomers are in the form of the pure antipodes and/or of racemates.

The compounds of formula I may also be employed in the form of their hydrates or include other solvents used for crystallisation.

The topically administrable pharmaceutical preparations according to the invention contain the pharmaceutically acceptable compounds of formula I, for example, in a pharmacologically effective amount, together with a pharmaceutically acceptable additive or adjunct. The daily dose of active ingredient depends on age and individual condition and on the method of administration.

Pharmaceutical preparations suitable for topical administration are especially creams, ointments and gels and also pastes, foams, tinctures and solutions that contain from approximately 0.5 to approximately 5% active ingredient.

Creams or lotions are oil-in-water emulsions that contain more than 50% water. As oily base there are used especially fatty alcohols, especially those containing from 12 to 18 carbon atoms, for example lauryl, cetyl or stearyl alcohol, fatty acids, especially those containing from 10 to 18 carbon atoms, for example palmitic or stearic acid, liquid to solid waxes, for example isopropyl myristate, wool wax or beeswax, and/or hydrocarbons, especially liquid, semi-solid or solid substances or mixtures thereof, for example petroleum jelly (petrolatum) or paraffin oil. Suitable emulsifiers are surface-active substances having predominantly hydrophilic properties, such as corresponding non-ionic emulsifiers, for example fatty acid esters of polyalcohols or ethylene oxide adducts thereof, especially corresponding fatty acid esters with (poly)ethylene glycol, (poly)propylene glycol or sorbitol, the fatty acid moiety containing especially from 10 to 18 carbon atoms, especially partial glycerol fatty acid esters or partial fatty acid esters of polyhydroxyethylene sorbitan, such as polyglycerol fatty acid esters or polyoxyethylene sorbitan fatty acid esters (Tweens), and also polyoxyethylene fatty alcohol ethers or fatty acid esters, the fatty alcohol moiety containing especially from 12 to 18 carbon atoms and the fatty acid moiety especially from 10 to 18 carbon atoms, especially those having approximately from 2 to 23 ethylene glycol or ethylene oxide units, such as polyhydroxyethylenecetylstearyl ether (for example Cetomacrogol), polyhydroxyethylene-(4)-lauryl ether and polyhydroxyethyleneglycerol fatty acid ester (for example Tagat S), or corresponding ionic emulsifiers, such as alkali metal salts of fatty alcohol sulfates, especially having from 12 to 18 carbon atoms in the fatty alcohol moiety, for example sodium lauryl sulfate, sodium cetyl sulfate or sodium stearyl sulfate, which are usually used in the presence of fatty alcohols, for example cetyl alcohol or stearyl alcohol. Additives to the aqueous phase are, inter alia, agents that prevent the creams from drying out, for example humectants, such as polyalcohols, such as glycerol, sorbitol, propylene glycol and/or polyethylene glycols, and also preservatives, perfumes, etc.

Ointments or lotions are water-in-oil emulsions that contain up to 70%, but preferably from approximately 20% to approximately 50%, water or aqueous phase. Suitable as fatty phase are especially hydrocarbons, for example petroleum jelly, paraffin oil and/or hard paraffins, which, in order to improve the water-binding capacity, preferably contain suitable hydroxy compounds, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the aqueous phase are, inter alia, humectants, such as polyalcohols, for example glycerol, propylene glycol, sorbitol and/or polyethylene glycol, and also preservatives, perfumes, etc.

Microemulsions are isotropic systems based on the following four components: water, an emulsifier, for example of the type indicated above, such as a surfactant, for example emulgin, a lipid, such as a non-polar oil, for example paraffin oil, and an alcohol containing a lipophilic group, for example 2-octyldodecanol. If desired, other additives may be added to the microemulsions.

Fatty ointments are water-free and contain as base especially hydrocarbons, for example paraffin, petroleum jelly and/or liquid paraffins, also natural or partially synthetic fat, such as fatty acid esters of glycerol, for example coconut fatty acid triglyceride, or preferably hardened oils, for example hydrogenated groundnut oil or castor oil, also fatty acid partial esters of glycerol, for example glycerol mono- and di-stearate, and also, for example, the fatty alcohols increasing the water-absorption capacity, emulsifiers and/or additives mentioned in connection with the ointments.

With gels, a distinction is made between aqueous gels, water-free gels and gels having a low water content, which gels consist of swellable, gel-forming materials. There are used especially transparent hydrogels based on inorganic or organic macromolecules. High molecular weight inorganic components having gel-forming properties are predominantly water-containing silicates, such as aluminium silicates, for example bentonite, magnesium aluminium silicates, for example Veegum, or colloidal silicic acid, for example Aerosil. As high molecular weight organic substances there are used, for example, natural, semi-synthetic or synthetic macromolecules. Natural and semi-synthetic polymers are derived, for example, from polysaccharides containing a great variety of carbohydrate components, such as celluloses, starches, tragacanth, gum arabic and agar-agar, and gelatin, alginic acid and salts thereof, for example sodium alginate, and derivatives thereof, such as lower alkylcelluloses, for example methyl- or ethyl-cellulose, carboxy- or hydroxy-lower alkylcelluloses, for example carboxymethyl- or hydroxyethyl-cellulose. The components of synthetic gel-forming macromolecules are, for example, suitably substituted unsaturated aliphatic compounds such as vinyl alcohol, vinylpyrrolidine, acrylic or methacrylic acid. Examples of such polymers are polyvinyl alcohol derivatives, such as polyviol, polyvinylpyrrolidines, such as collidone, polyacrylates and polymethacrylates, especially having a molecular weight of from approximately 80000 to approximately 1 million, or salts thereof, such as Rohagit S, Eudispert or Carbopol. Customary additives, such as preservatives or perfumes, may be added to the gels.

Foams are administered, for example, from pressurised containers and are liquid oil-in-water emulsions in aerosol form; unsubstituted or halogenated hydrocarbons, such as alkanes, for example propane or butane, or chlorofluoro-lower alkanes, for example dichlorodifluoromethane and dichlorotetrafluoroethane, are used as propellant. As oil phase there are used, inter alia, hydrocarbons, for example paraffin oil, fatty alcohols, for example cetyl alcohol, fatty acid esters, for example isopropyl myristate, and/or other waxes. As emulsifiers there are used, inter alia, mixtures of emulsifiers having predominantly hydrophilic properties, such as polyoxyethylene sorbitan fatty acid esters (Tweens), and emulsifiers having predominantly lipophilic properties, such as sorbitan fatty acid esters (Spans). The customary additives, such as preservatives, etc., are also added.

Tinctures and solutions generally have an ethanolic base, to which water may be added and to which there are added, inter alia, polyalcohols, for example glycerol, glycols and/or polyethylene glycol, as humectants for reducing evaporation, and fat-restoring substances, such as fatty acid esters with low molecular weight polyethylene glycols, that is to say lipophilic substances that are soluble in the aqueous mixture, as a replacement for the fatty substances removed from the skin by the ethanol, and, if necessary, other adjuncts and additives. Suitable tinctures or solutions may also be applied in spray form by means of suitable devices.

The manufacture of the topically administrable pharmaceutical preparations is effected in a manner known per se, for example by dissolving or suspending the active ingredient in the base or, if necessary, in a portion thereof. When the active ingredient is administered in the form of a solution, it is generally dissolved in one of the two phases before emulsification; when the active ingredient is administered in the form of a suspension, it is mixed with a portion of the base after emulsification and then added to the remainder of the formulation.

The present invention relates especially to multi-layered therapeutic systems for the transdermal administration of pharmaceutically acceptable methanediphosphonic acid derivatives, especially those of formula I, and their salts, which contain essentially the following constituents:
(1) a closed backing foil which is impermeable to the subsequent layers of the constituents of the active ingredient formulation,
(2) a reservoir for the active ingredient, next to the backing foil, provided that the active ingredient is not already present in the adhesive foil,
(3) an adhesive layer and
(4) a peel-off protecting foil.

The therapeutic system according to the invention for the transdermal administration of methanediphosphonic acid derivatives of formula I is preferably in the form of a plaster having a base surface that is at least as large in area as the area of the skin envisaged for the administration and at least as is large as is required for it to stay firmly in place over the entire period of treatment. The base surface must be large enough for sufficient quantities of the active constituents of the active ingredient formulation (for example, active ingredient and the agents for enhancing percutaneous absorption, hereinafter "penetration enhancers") to be absorbed by the skin. Although, in theory, very large areas of skin are available for taking the plaster, for reasons of comfort the wanted surface area of the base surface of the plaster is about 200 cm$^2$, in the first line about 20 to about 30 cm$^2$.

The plaster may be of any geometrical shape, e.g. may be oval, elliptical, circular, rectangular, optionally with rounded corners, oblong or rectangular with one or two rounded tabs. Other shapes are also possible.

The backing foil (1) consists of a material or of a combination of materials that must be impermeable to the constituents of the formulation contained in the reservoir (2). It serves as a protecting and supporting layer. To produce the backing foil, it is possible to use high or low pressure polymers such as polyethylene, polypropylene, polyvinyl chloride, polyethylene terephthalate or also cellulose acetate or vinyl acetate/vinyl chloride copolymers and combinations, especially composite foils thereof. An impermeable, flexible backing foil that conforms to the shape of the part of the body to which the plaster is applied and that consists of materials suitable for the manufacture of hot form-sealed systems is preferred.

The reservoir (2) for the active ingredient is situated between the backing foil (1) and the adhesive layer (3), which in turn is arranged on the peel-off protecting foil (4), and contains all essential constituents of the active ingredient formulation. The reservoir serves to hold the active ingredient in a limited space for release to the skin. It may contain a liquid, semi-solid or solid active ingredient formulation or may formed as homogeneous or inhomogeneous polymer matrix containing itself the active ingredients. Preferably, the reservoir layer containing the active ingredient is formed as adhesive matrix which in case of a monolith system needs no additional adhesive layer. In an other preferred embodiment as reservoir a liquid or semi-solid composition which contains the active ingredient and which may melt a skin temperature is embedded in a non-woven fabric or in a polymeric foam.

However, if the reservoir is not itself the adhesive matrix or is incorporated in an adhesive layer, it can be bonded to an adhesive layer, which in turn can be bonded to the peel-off layer. Furthermore, a porous or permeable membrane may be arranged between the reservoir and an adhesive layer which in turn is arranged on a peel-off layer (4).

For example, an arrangement in which the reservoir is in firm contact with the skin is known per se and is described, for example, in British Patent Application 2,021,950. The area of the backing foil (1) is greater than the area occupied by the reservoir (2) and, therefore, the backing foil projects beyond the reservoir, the projecting portion of the backing foil (1) being provided with an adhesive layer and adhering to the skin. The peel-off protective layer (4) lies over the adhesive layer (3) and over the reservoir (2), it being possible for the latter also to be limited by an additional membrane.

An example of a system in which the reservoir (2) is, for example, in firm contact with the adhesive layer (3), it being possible for the active ingredient base to be present both in the reservoir and in the adhesive layer, is described in U.S. Pat. No. 4,597,961. The backing foil (1) is also larger in area than the area occupied by the reservoir (2) and projects beyond the latter. The adhesive layer (3) covers both the reservoir (2) and the projecting portion of the backing foil (1). The peel-off protective layer (4) lies on top of the adhesive layer.

The matrix used for immobilising drug compositions which are liquid or semi-solid or which melt at skin temperature essentially consists of, for example, natural or synthetic polymers, such as cotton, cellulose, regenerated cellulose, polyamides, polyester, polyurethane or cellulose derivatives, for example those of the type described below, viscose or polypropylene. In particular, such fibrous structures are used in the form of a non-woven fabric or in form of woven and mitted fabrics and also foams.

The reservoir (2) can also contain liquid polymeric material in which the active ingredient formulation or constituents thereof are homogeneously dispersed. Such polymeric materials are, for example, silicone rubber (silicones), e.g. linear organosiloxanes in which every silicon atom in the siloxane chain is substituted by two identical or different alkyl, e.g. methyl or ethyl, aryl, e.g. phenyl, alkenyl, e.g. vinyl or allyl, alkylaryl, e.g. tolyl or xylyl, or aralkyl, e.g. benzyl, radicals, and every terminal silicon atom is substituted by three of the mentioned organic radicals. The preparation of these silicones is described in U.S. Pat. Nos. 2,541,137, 2,723,966, 2,863,846, 2,890,188, 2,927,907, 3,002,951 and 3,035,016.

In addition to the liquid polymeric material and the active ingredient formulation, the reservoir (2) can also contain other liquids such as glycerol or propylene glycol and also water and have the release properties described in U.S. Pat. No. 4,291,015.

The contents of the reservoir (2) preferably consist exclusively of the actual active ingredient formulation which contains the penetration enhancer, especially ethanol, the active ingredient and, optionally, other auxiliaries, for example gelling agents and, optionally, viscosity-increasing adjuncts, such as polyvinyl alcohol, polyvinylpyrrolidone, cellulose derivatives, e.g. those of the type mentioned, and gelatin.

The reservoir (2) can, in addition, be provided with a permeable layer of the required permeability to the active ingredient and the penetration enhancer. This layer controls the rate of release of the penetration enhancer and/or of the active ingredient from the system to the skin and is also called a control or regulating membrane.

The materials that can be used in the therapeutic systems of the invention for producing the permeable layer are known per se. Such membrane materials may be homogeneous (diffusion membranes) or macrostructured (porous membranes). The latter may be regarded as being a sponge-like structure having a skeleton of polymeric material with interconnected voids and pores dispersed therein. Membrane materials that control the rate of release may consist of isotropic material with a homogeneous structure or of anisotropic material with a non-homogeneous structure. Such materials are commercially available and can be produced in various ways, for example as described by R. E. Kesting, Synthetic Polymer Membranes, McGraw Hill, Chapters 4 and 5, 1971, J. D. Ferry, Ultrafiltration Membranes, Chemical Review, Vol. 18, page 373, 1984.

Membrane materials having from 5 to 95% by volume voids and an effective pore diameter of approximately from $1.0 \times 10^{-9}$ m to $1.0 \times 10^{-4}$ m are especially suitable. More especially suitable are membrane materials having pore diameters of less than approximately $5.0 \times 10^{-9}$ m and molecular diffusion. For best results, reference should be made to the prior art and the known embodiments with known membrane materials and known shapes which ensure an optimum rate of release of the active ingredient. In particular, the membrane material must be chemically resistant to the active ingredient and to the penetration enhancer used.

A list of suitable membrane materials, which should not be regarded as exhaustive, is given below:

polycarbonates, e.g. linear polyesters of carbonic acid derivatives that contain carbonate groups in the polymer chain and can be prepared, for example, by reacting dihydroxy aromatic compounds with phosgene. Such materials are obtainable from General Electric under the trade mark Lexan ®;

polyvinyl chlorides, e.g. PVC, which is obtainable from Goodrich under the trade mark Geon ® 121;

polyamides of the polyhexamethyleneadipamide type, or polyamides known by the generic name "Nylon". An especially suitable material is sold under the trade mark Nomex ® by DuPont;

acrylic acid copolymers, e.g. those which are sold under the trade name Dynel ® and consist of about 60% polyvinyl chloride and 40% acrylonitrile, and styrene/acrylic acid copolymers and the like;

polysulfones with diphenylsulfone groups in the linear chain. Such polymers are sold as P-1700 by Union Carbide;

halogenated polymers, such as polyvinylidene fluorides, that are sold, for example, under the trade mark Kynar ® by Pennwalt; polyvinyl fluorides that are obtainable from DuPont under the trade mark Tedlar ®, and polyfluorohalocarbons obtainable under the trade mark Aclar ® from Allied Chemical;

polychloroethers that are sold by Hercules under the trade mark Penton ®, and other similar thermoplastic polymers;

acetal polymers such as the polyformaldehyde polymers that are sold by DuPont under the trade mark Delrin ®, and the like;

acrylic acid resinates, such as polymethyl methacrylate, poly-n-butyl methacrylate and the like;

polyethylene and copolymers of ethylene, e.g. with vinyl acetate or acrylates.

other polymers, such as polyurethanes, polyimides, polybenzimidazoles, polyvinyl acetate, aromatic and aliphatic polyethers, cellulose esters, for example cellulose triacetate, cellulose, Colledion ® (cellulose nitrate with 11% nitrogen), epoxy resinates, polyolefins, e.g. polyethylene/polypropylene, porous rubber, polyvinylpolypyrrolidone, crosslinked polyvinyl alcohol, copolymers of vinylpyrrolidone and vinyl alcohols, polyelectrolyte structures consisting of two ionically associated polymers as are described in U.S. Pat. Nos. 3,549,016 and 3,546,142, polystyrene derivatives such as polystyrene sodium sulfonates or polyvinylbenzyltrimethylammonium chlorides, polyhydroxyethyl methacrylates, polyisobutyl vinyl ether and similar polymers can also be used. Other copolymers that are obtainable by copolymerisation of various amounts of the monomers forming the basis of the mentioned polymers can also be used to produce the membrane material determining the rate of release of the active ingredient and/or the penetration enhancer.

When using a permeable membrane, several arrangements are possible: the active ingredient formulation is arranged between the backing foil (1) and the membrane layer. In that arrangement, the backing foil and the membrane form a space which can optionally be divided into several compartments. In certain embodiments, the backing foil (1) and the membrane layer are joined, e.g. welded or glued, to each other at the very edge. In these embodiments, the active ingredient and the penetration enhancer are contained in the same reservoir. These embodiments are preferred when the active ingredient formulation is liquid or semi-solid.

It is also possible, in accordance with the embodiment described in German Offenlegungsschrift 3,205,258, to fill the space formed by the backing foil (1) and the membrane only with penetration enhancer, e.g. ethanol, and optionally with a gelling agent or viscosity-increasing adjunct, such as gelatin, and to apply the active ingredient formulation to the other side of the membrane. In that case, the membrane would control only the rate of diffusion of the enhancer. The active ingredient can be present in a separate layer between membrane and adhesive layer (3) and optionally or exclusively in the adhesive layer (3).

The reservoir (2) can, in addition, be divided into several compartments. This division into compartments is suitable for liquid active ingredient formulations and prevents the latter from sinking and becoming concentrated at the lowest point of the system if cavities or folds are formed as a result of the plaster not being stored flat. Division into compartments is especially advantageous if the reservoir layer occupies an area of more than 30 cm$^2$. The compartments can be distributed as desired. For example, a radial arrangement of the partitions, extending from the middle point of the plaster, or vertical or horizontal boundaries, or oblique lines etc. are possible.

Division of the compartments, especially by partitions or seal seams, can be effected by hot-welding. In this procedure, the material of the backing foil (1) is welded to the material of the membrane layer.

Dermatologically acceptable adhesives are suitable for the adhesive layer (3). Suitable adhesives are, for example, silicone adhesives [e.g. of the Bio-PSA ® or Silicon Adhesive 355 (Dow Corning) type], adhesive formulations of acrylic acid resins or methacrylic acid resins, e.g. polymers of acrylic acid or methacrylic acid esterified by alcohols such as n-butanol, n-pentanol, isopentanol, 2-methylbutanol, 1-methylbutanol, 1-, 2- or 3-methylpentanol, 2-ethylbutanol, isooctanol, n-decanol or n-dodecanol, or copolymers of these acrylic acid or methacrylic acid esters with monomers containing ethylene groups, such as acrylic acid itself, methacrylic acid, acrylamide, methacrylamide, N-alkoxymethacrylamide, N-alkoxymethylmethacrylamide, N-tert.-butylamide, itaconic acid, vinyl acetate [e.g. of the Durotak ® 280-2516 type (National Starch & Chemical B.V.)], N-branched alkylmaleic acid amide in which the branched alkyl group has from 10 to 24 carbon atoms, glycol diacrylates or mixtures thereof, polyalkenylenes, such as polyisobutylenes of different molecular weights, for example of from approximately 100 to 1.5 million, e.g. polyisobutylene 300 or 35000 or 1.2 million, hydrogenated hydrocarbon resins, natural or synthetic rubber, such as styrenebutadiene, butyl ether, neoprene, polyisobutylene, polybutadiene and polyisoprene, polyvinyl acetate, urea/formaldehyde resinates, resorcinol/-formaldehyde resinates, cellulose derivatives such as ethylcellulose, methylcellulose, nitrocellulose, cellulose acetate butyrate and carboxymethylcellulose, and also natural gums such as agar, acacia, pectin, starch, dextrin, albumin, gelatin, casein, etc. It is also possible to add thickeners and stabilisers and also solvents to the mentioned adhesives; however, they may be used without solvents in the form of so-called hot-melt adhesives, which are applied at higher temperatures to the polymeric materials in the molten state. The solvents in which the adhesives are dissolved are, especially, are readily volatile and tolerated by the skin. Examples that may be mentioned are corresponding hydrocarbons, such as alkanes, e.g. hexane, heptane, aromatic hydrocarbons, e.g. toluene, lower alkanols, such as methanol, ethanol or isopropanol, esters, such as lower alkanecarboxylic acid-lower alkyl esters, e.g. ethyl acetate, or ketones, such as acetyl acetone, or mixtures thereof.

The adhesive layer (3) may be applied to some or all of the membrane. If the membrane is completely covered by the adhesive layer, the latter may, in addition to its actual function as an adhesive to the skin, act as a permeable membrane. The desired membrane properties, e.g. control of the rate of diffusion of the penetration enhancer, can be obtained by varying the thickness and composition of the adhesive layer (3). The adhesive layer (3) may, in addition, contain the total amount or, preferably, a portion of the active ingredient. The amount of active ingredient contained in the adhesive layer (3) can be used, in particular, to administer an initial surge dose before the continuous release, which is controlled by the therapeutic system, commences at the desired therapeutic level.

The membrane can also be covered by the adhesive layer (3) partially and/or discontinuously. A covering at the edges is possible, for example an annular circumferential covering. The membrane can also be covered in a pattern, for example in a rhomboidal pattern. The membrane can be covered at the outer edge by a continuous band of adhesive material, for example in the shape of a ring, and on the inside surface with discontinuous bands, for example in a rhomboidal pattern.

The protective layer (4) is removed before application. It consists of materials that are impermeable to the constituents of the reservoir layer (2). It is possible to use the same materials as those used for producing the backing foil (1), and also metal foils, for example thin aluminium foil. Organic polymers are rendered capable of being peeled off the adhesive layer, for example, by suitable surface treatment, for example silicone treatment.

The active ingredient formulation contained in the transdermal therapeutic system of the invention, especially in the reservoir (2), contains as adjunct an agent that enhances percutaneous absorption (penetration enhancer—"flux-enhancer") which increases the flux of the active ingredients of formula I through the skin, so that a greater quantity of active ingredients is absorbed by the skin per unit of application area and per unit of time. The penetration enhancer can, in addition, accelerate the flow of the active ingredient through the permeable membrane layer in membrane systems. In particular, the use of a suitable penetration enhancer results in the administration through the skin of that dosage of active ingredients which is required per unit of time to maintain the therapeutic level. Suitable penetration enhancers have a higher flux through the skin than do the active ingredients whose absorption is to be enhanced and can be mixed with other pharmaceutically acceptable adjuncts.

Suitable penetration enhancers are preferably monovalent, saturated or unsaturated aliphatic, cycloaliphatic or aromatic alcohols having from 4 to 12 carbon atoms, e.g. n-hexanol or cyclohexanol, aliphatic, cycloaliphatic or aromatic hydrocarbons having from 5 to 12 carbon atoms, e.g. hexane, cyclohexane, isopropylbenzene and the like, cycloaliphatic or aromatic aldehydes and ketones having from 4 to 10 carbon atoms, such as cyclohexanone, acetamide, N,N-di-lower alkylacetamides such as N,N-dimethylacetamide or N,N-diethylacetamide, $C_{10}$–$C_{20}$alkanoylamides, e.g. N,N-dimethyllauroylamide, 1-n-$C_{10}$–$C_{20}$alkylazacycloheptan-2-one, e.g. 1-n-dodecylazacycloheptan-2-one (Azone ®, Nelson), pyrrolidones, such as N-methylpyrrolidone, polyalkylene glycol laureates, e.g. polyethylene glycol monolaureate or N-2-hydroxyethylacetamide, and known vehicles and/or penetration enhancers such as aliphatic, cycloaliphatic and aromatic esters, N,N-di-lower alkyl sulfoxide, unsaturated oils, halogenated or nitrated aliphatic or cycloaliphatic hydrocarbons, salicylates, polyalkylene glycol silicates, and mixtures thereof.

$C_2$–$C_4$alkanols, e.g. isopropanol or isobutanol and, especially, ethanol, are especially preferred as penetration enhancers.

The amount of active ingredient, present in the therapeutic system, that is required to achieve a therapeutic effect depends on many factors: inter alia the minimum necessary dosage, the permeability of the membrane material, which determines the flux, and of the adhesive layer, and the period for which the plaster will be fixed to the skin or the mucous membranes. Since the active ingredient is to be released over a period of more than one day, there is, in fact, no upper limit to the maximum amounts of active ingredient present in the plaster. The minimum amount of active ingredient is determined by the requirement that sufficient, for example therapeutically effective, quantities of active ingredient must be present in the plaster to maintain the desired rate of release over the given period.

Adjuncts can be added to the active ingredients. Suitable adjuncts are water, isotonic aqueous sodium chloride solution, dextrose in water or sodium chloride solution, liquid glyceryl triesters with low molecular weight fatty acids, lower alkanols, natural oils such as corn oil, groundnut oil, sesame oil, castor oil and condensation products thereof with ethylene oxide, and the like, hydrocarbons such as pharmaceutical grade mineral oil, silicones, emulsifiers such as monoglycerides or diglycerides of fatty acids, phospholipic acid derivatives such as lecithin or cephalin, polyalkylene glycols such as polyethylene glycol, aqueous phases to which a swelling agent such as sodium carboxymethylcellulose, sodium alginate, polyvinylpolypyrrolidone, etc. has been added and to which, in addition, dispersion agents or emulsifiers such as lecithin may be added, polyoxyethylene and the like. The adjuncts may, in addition, contain additives such as preservatives, stabilisers, wetting agents, emulsifiers, etc.

If $C_2$–$C_4$alkanols such as ethanol are used as penetration enhancers, gelling agents such as gelatin or swelling agents such as cellulose ethers, e.g. hydroxypropylcellulose, are preferably added as adjuncts to the active ingredient formulation.

The transdermal therapeutic systems of the invention are prepared in a manner known per se, for example as follows: the adhesive layer (3) is applied to a base layer (peel-off protective layer (4)), e.g. foil or film. The constituents of the active ingredient reservoir, for example membrane layer and active ingredient formulation, can also be applied to the base layer, and the impermeable backing foil can be placed on top. The plaster is then punched out of the master. The reservoir is optionally bonded to the backing foil with additional adhesive. The reservoir can also be hot-welded to the membrane or to the adhesive. In liquid-filled systems, the membrane layer is applied to the adhesive layer and the active ingredient formulation is placed on the membrane.

The preparation processes are described in U.S. Pat. No. 3,797,494, preferably in DE-A-26 04 718 and DE-A-32 05 258 and in U.S. Pat. Nos. 4,031,894 and 4,262,003 or in the publication by H. Asche in Schweiz. Rundschau Med. (Praxis) 74, No. 11,257–260 (1985), but the use according to the invention is not limited to the transdermal therapeutic systems described in those publications. The preferred transdermal therapeutic system described in DE-A 32 05 258 is a therapeutic system in the form of a plaster-like patch that releases the active ingredient transdermally, avoiding side-effects, and delivers it through the skin so that the active ingredient content of the plasma remains approximately constant.

The daily dose of active ingredient for a patient weighing about 70 kg is estimated to be from approximately 50 µg to approximately 150 µg, depending on the potency of the particular active ingredient used.

The following Examples illustrate the invention described above, but they do not limit the scope thereof in any way.

EXAMPLE 1

Gel, containing as active ingredient, for example, 3-amino-1-hydroxypropane-1,1-diphosphonic acid, having the following composition:

| | |
|---|---|
| active ingredient | 1.0 g |
| Carbopol 934 P | 1.0 g |
| glycerol | 3.0 g |
| isopropanol | 25.0 g |
| Softigen 767 | 0.2 g |
| demin. water q.s. ad | 100.0 g |

EXAMPLE 2

Solution, containing as active ingredient, for example, 3-amino-1-hydroxypropane-1,1-diphosphonic acid, having the following composition:

| | |
|---|---|
| active ingredient | 1.0 g |
| isopropanol | 60.0 g |
| propylene glycol | 10.0 g |
| demin. water q.s. ad | 100.0 g |

EXAMPLE 3

Microemulsion, containing as active ingredient, for example, 3-amino-1-hydroxypropane-1,1-diphosphonic acid, having the following composition:

| active ingredient | 1.0 g |
|---|---|
| Labrasol* | 32.9 g |
| Plurolisostearate** | 13.2 g |
| isostearyl isostearate | 41.9 g |
| demin. water q.s. ad | 100.0 g |

EXAMPLE 4

Cream (W/O), containing as active ingredient, for example, 3-amino-1-hydroxypropane-1,1-diphosphonic acid, having the following composition:

| active ingredient | 1.0 g |
|---|---|
| cetyl alcohol | 6.5 g |
| cetyl palmitate | 5.0 g |
| stearyl alcohol | 6.5 g |
| petroleum jelly | 5.0 g |
| glycerol | 12.5 g |
| sodium laurylsulfate | 1.0 g |
| methylparaben | 0.18 g |
| propylparaben | 0.05 g |
| demin. water q.s. ad | 100.0 g |

EXAMPLE 5

Ointment (O/W emulsion), containing as active ingredient, for example, 3-amino-1-hydroxypropane-1,1-diphosphonic acid, having the following composition:

| active ingredient | 1.0 g |
|---|---|
| cetyl alcohol | 3.0 g |
| glycerol | 6.0 g |
| methylparaben | 0.18 g |
| propylparaben | 0.05 g |
| Arlacel 60 | 0.6 g |
| Tween 60 | 4.4 g |
| stearic acid | 9.0 g |
| isopropyl palmitate | 2.0 g |
| paraffin oil, viscous | 10.0 g |
| demin. water q.s. ad | 100.0 g |

EXAMPLE 6

Anhydrous ointment, containing as active ingredient, for example, 3-amino-1-hydroxypropane-1,1-diphosphonic acid, having the following composition:

| active ingredient | 1.0 g |
|---|---|
| petroleum jelly | 35.0 g |
| paraffin oil, viscous | 35.0 g |
| Lanette N | 30.0 g |

EXAMPLE 7

Lotion, containing as active ingredient, for example, 3-amino-1-hydroxypropane-1,1-diphosphonic acid, having the following composition:

| active ingredient | 1.0 g |
|---|---|
| cetyl alcohol | 1.9 g |
| glycerol | 4.3 g |
| sodium laurylsulfate | 1.0 g |
| methylparaben | 0.18 g |

-continued

| propylparaben | 0.05 g |
|---|---|
| paraffin oil, viscous | 2.5 g |
| demin. water q.s. ad | 100.0 g |

EXAMPLE 8

Foam, containing as active ingredient, for example, 3-amino-1-hydroxypropane-1,1-diphosphonic acid, having the following composition:

| active ingredient | 1.0 g |
|---|---|
| cetyl alcohol | 1.7 g |
| glycerol | 5.0 g |
| methylparaben | 0.18 g |
| propylparaben | 0.05 g |
| isopropyl palmitate | 2.0 g |
| Arlacel 83 | 1.5 g |
| Cetomacrogol 1000 | 2.4 g |
| paraffin oil, viscous | 1.0 g |
| demin. water q.s. ad | 100.0 g |

EXAMPLE 9

Monolith adhesive transdermal system, containing as active ingredient, for example, 3-amino-1-hydroxypropane-1,1-diphosphonic acid

| Composition: | |
|---|---|
| polyisobutylene (PIB) 300 (Oppanol B1, BASF) | 5.0 g |
| PIB 35000 (Oppanol B10, BASF) | 3.0 g |
| PIB 1200000 (Oppanol B100, BASF) | 9.0 g |
| hydrogenated hydrocarbon resin (Escorez 5320, Exxon) | 43.0 g |
| 1-dodecylazacycloheptan-2-one (Azone, Nelson Res., Irvine CA) | 20.0 g |
| active ingredient | 20.0 g |
| Total | 100.0 g |

Preparation

The above components are together dissolved in 150 g of special boiling point petroleum fraction 100–125 by rolling on a roller gear bed. The solution is applied to a polyester film (Hostaphan, Kalle) by means of a spreading device using a 300 μm doctor blade, giving a coating of about 75 g/m². After drying (15 minutes at 60° C.), a silicone-treated polyester film (thickness 75 μm, Laufenberg) is applied as the peel-off film. The finished systems are punched out in sizes in the wanted form of from 5 to 30 cm² using a punching tool. The complete systems are sealed individually in sachets of aluminised paper.

EXAMPLE 10

Matrix transdermal system with adhesive coating at the edge only, containing as active ingredient, for example, 3-amino-1-hydroxypropane-1,1-diphosphonic acid

| Composition: | |
|---|---|
| active ingredient | 10.0 g |
| hydroxypropylcellulose (Klucel HF) | 1.0 g |
| polyethylene glycol monolaurate | 5.0 g |

-continued

| Composition: | |
|---|---|
| demineralised water | 84.0 g |

Preparation

The constituents are dissolved in water, with stirring. A polyester film (Hostaphan, Kalle) is coated with silicone adhesive (Silicon Adhesive 355, Dow Corning, 55% solid dissolved in special boiling point petroleum fraction 100–120) using a spreading device and a 150 μm doctor blade, and is then dried (15 minutes, 60° C.).

Discs having a diameter of 2.5 cm (corresponding to a surface area of 5 cm$^2$) are punched out of a non-woven fabric of viscose, polyamide and polypropylene (Vilmed type M 1539, Freudenberg) having a thickness of about 2.7 mm. After these discs have been bonded to the coated side of the polyester film, the above solution is metered onto the fabric discs in an amount of 450 mg per system by means of a micro-metering system. The discs are then covered with a silicone-treated polyester film. The individual systems are punched out using a tool having a diameter of 5 cm, care being taken to ensure that the fabric disc charged with the active ingredient solution is located in the centre of the system. The finished systems are packed individually as described in Example 9.

EXAMPLE 11

Membrane transdermal system, closed by means of a seal seam at the edge and containing as active ingredient, for example, 3-amino-1-hydroxypropane-1,1-diphosphonic acid

| Composition: | |
|---|---|
| active ingredient | 10.0 g |
| hydroxypropylcellulose (Klucel HF) | 1.0 g |
| polyethylene glycol monolaurate | 5.0 g |
| demineralised water | 84.0 g |

Preparation

The adhesive layer (silicone adhesive, see Example 10 is applied to a fluorine-treated polyester film by means of a screen printing process and dried. Application of a heatsealable non-woven fabric of cellulose and polyester (Sontara Vlies 8412, DuPont) to form a laminate consisting of the peel-off film, the adhesive layer and the fabric. The solution is applied by means of a micro-metering system to the above laminate (fabric on top) in an amount of 300 mg for a 5 cm$^2$ system, a cover film of a heat-sealable polyester/ethyl vinyl acetate composite foil (Scotchpack 1220, 3M) is drawn over the laminate (ethyl vinyl acetate side towards the solution or fabric), and the system is sealed using a suitable heat-sealing tool (inside diameter 2.5 cm, outside diameter 3.5 cm; sealing conditions: 0.5 sec, 170° C.) and then punched out and packed individually as described in Example 9.

EXAMPLE 12

System analogous to Example 11

| Composition: | |
|---|---|
| active ingredient | 10.0 g |
| hydroxypropylcellulose (Klucel HF) | 3.0 g |
| 1-dodecylazacycloheptan-2-one (Azone, Nelson Res., Irvine CA) | 5.0 g |
| ethanol 50% | 84.0 g |

Preparation

The constituents are dissolved by stirring. Preparation and packing of the systems analogously to Example 11.

In a manner analogous to that described in any one of the above Examples, it is possible to incorporate into the base layers other active ingredients of formula I, for example selected from 3-amino-1-hydroxypropane-1,1-diphosphonic acid, 3-dimethylamino-1-hydroxypropane-1,1-diphosphonic acid and 3-(N-methyl-N-n-propylamino)-1-hydroxypropane-1,1-diphosphonic acid, or a pharmaceutically acceptable salt thereof.

EXAMPLE 13

Matrix transdermal system consisting of two layers and containing as active ingredient, for example, 3-amino-1-hydroxypropane-1,1-diphosphonic acid Layer 1:

Identical to the matrix of Example 9, the matrix being applied by means of a 150–250 μm doctor blade (rate of application 30–60 g/m$^2$) to a silicone-treated polyester film (for specifications see Example 9) and covered with a silicone-treated paper foil (temporary covering).

Layer 2:

A suitable amount of flux enhancer (e.g. 5–25% 1-dodecylazacycloheptan-2-one, Azone) is dissolved in the adhesive compound specified in Example 9 (dissolved in benzine) or in another suitable adhesive (e.g. copolymer based on acrylate esters and vinyl acetate, Durotak 280-2516, National Starch & Chemical BV, Zutphen/NL) without the active ingredient. The adhesive is laminated by means of a 150–300 μm doctor blade and the intermediate layer is removed continously and discarded. Further processing as in Example 9.

EXAMPLE 14

Matrix transdermal system consisting of two layers and containing as active ingredient, for example, 3-amino-1-hydroxypropane-1,1-diphosphonic acid Layer 1:

As Example 13.

Layer 2:

A suitable amount of flux enhancer is introduced into a customary hot-melt adhesive (e.g. acrylate adhesive Durotak 089-1526). A polyester film is applied with an aluminium foil by means of a hot-melt applicator at about 140°–160° C. The further processing of layers 1 and 2 is carried out as in Example 13.

EXAMPLE 15

Reservoir-type membrane transdermal system, containing as active ingredient, for example, 3-amino-1-hydroxypropane-1,1-diphosphonic acid Composition analogous to Example 11.

Onto the membrane side of a laminate consisting of peel-off film (polyester, silicone-treated on one side, thickness about 75 μm;) adhesive (e.g. suitable mixture of polyisobutylene 1200000, polyisobutylene 35000 and polyisobutylene 1200; rate of application 40–60 g/m$^2$); regulation membrane (ethyl vinyl acetate containing 6–25% vinyl acetate, preferably 12–18%, thickness about 50 μm) an amount of about 100–600 mg, depending on the system area provided, of the reservoir formulation according to Example 18 is metered on a suitable apparatus.

Alternatively, the active ingredient, or a portion thereof, can be dissolved or suspended in the adhesive layer. In that case, the active ingredient contained in the adhesive layer would act as the initial dose and that in the reservoir as the maintenance dose.

In a manner analogous to that described in any one of the above Examples, it is possible to incorporate into the base layers other active ingredients of formula I, for example selected from 3-amino-1-hydroxypropane-1,1-diphosphonic acid, 3-dimethylamino-1-hydroxypropane-1,1-diphosphonic acid and 3-(N-methyl-N-n-propylamino)-1-hydroxypropane-1,1-diphosphonic acid, or a pharmaceutically acceptable salt thereof.

We claim:

1. A pharmaceutical preparation in the form of a multi-layered therapeutic system for transdermal administration containing a pharmaceutically acceptable methanediphosphonic acid derivative of formula

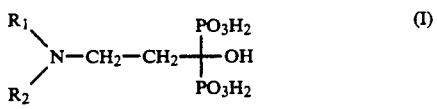

or a pharmaceutically acceptable salt thereof, wherein $R_1$ and $R_2$ are hydrogen or $C_1$–$C_3$ alkyl wherein the said multi-layered therapeutic system contains the following constituents:

(1) a polymer closed backing foil which is impermeable to the subsequent layers of the constituents of the active ingredient formulation, (2) a reservoir for the active ingredient, next to the backing foil, provided that the active ingredient is not already present in the adhesive foil, (3) an adhesive layer and (4) a peel-off protecting foil.

2. A pharmaceutical preparation according to claim 1, containing 3-amino-1-hydroxypropane-1,1-diphosphonic acid or a pharmaceutically acceptable salt thereof.

3. A pharmaceutical preparation according to claim 1, containing 3-dimethylamino-1-hydroxypropane-1,1-diphosphonic acid or a pharmaceutically acceptable salt thereof.

4. A pharmaceutical preparation according to claim 1, containing 3-(N-methyl-N-n-propylamino)-1-hydroxypropane-1,1-diphosphonic acid or a pharmaceutically acceptable salt thereof.

5. A pharmaceutical preparation according to claim 1 in the form of a matrix transdermal system in which the reservoir layer containing the active ingredient is formed as adhesive matrix or of a membrane transdermal system in which a porous or permeable membrane is arranged between the reservoir and the adhesive layer.

6. A method for the treatment of hypercalcaemia and osteolytic bone metastases which comprises administering to a warm-blooded animal including man in need thereof a pharmaceutical composition claim 1 as claimed in claims.

* * * * *

UNITED STATES PATENT AND TRADEMARK OFFICE
CERTIFICATE OF CORRECTION

PATENT NO. : 5,139,786

DATED : August, 18, 1992

INVENTOR(S) : PIER G. FERRINI, CARLO VOELLMY. PETER H. STAHL
JONATHAN GREEN

It is certified that error appears in the above-identified patent and that said Letters Patent is hereby corrected as shown below:

Column 18, line 33-34 delete both lines and replace with --thereof a pharmaceutical composition as claimed in claim 1.--

Signed and Sealed this

Twelfth Day of October, 1993

Attest:

BRUCE LEHMAN

*Attesting Officer*  *Commissioner of Patents and Trademarks*